(12) United States Patent
Childers

(10) Patent No.: US 8,206,696 B2
(45) Date of Patent: Jun. 26, 2012

(54) ANTIMICROBIAL SKIN PREPARATION

(75) Inventor: David Alan Childers, Huntington, WV (US)

(73) Assignee: Aplicare, Inc., Meriden, CT (US)

( * ) Notice: Subject to any disclaimer, the term of this patent is extended or adjusted under 35 U.S.C. 154(b) by 664 days.

(21) Appl. No.: 10/248,242

(22) Filed: Dec. 30, 2002

(65) Prior Publication Data

US 2004/0126355 A1 Jul. 1, 2004

(51) Int. Cl.
*A61K 31/79* (2006.01)
*A61K 33/36* (2006.01)
*A61K 47/32* (2006.01)

(52) U.S. Cl. .................. 424/78.24; 424/667; 514/772.5

(58) Field of Classification Search ............... 424/78.24, 424/667; 514/772.5
See application file for complete search history.

(56) References Cited

U.S. PATENT DOCUMENTS

| | | | |
|---|---|---|---|
| 4,584,192 A | 4/1986 | Dell | |
| 5,137,718 A | 8/1992 | Gillespie | |
| 5,695,458 A * | 12/1997 | Shikani et al. | 604/4.01 |
| 5,705,532 A * | 1/1998 | Modak et al. | 514/635 |
| 5,916,882 A | 6/1999 | Jeng | |
| 5,922,314 A | 7/1999 | Hoang | |
| 6,228,354 B1 * | 5/2001 | Jeng | 424/78.07 |
| 2002/0035046 A1 * | 3/2002 | Lukenbach et al. | 510/122 |
| 2002/0064544 A1 * | 5/2002 | Lezdey et al. | 424/407 |
| 2004/0052746 A1 * | 3/2004 | Tamareselvy et al. | 424/70.11 |

OTHER PUBLICATIONS

Caustics: Poison Control Center. Children's Hospital of Philadelphia. Accessed online on Sep. 17, 2008 at http://www.chop.edu/consumer/jsp/division/generic.jsp?id=70980.*
Aculyn TM 22 Product Brochure. Rohm and Haas. Accessed online on Sep. 17, 2008 at https://ecenter.rohmhaas.com/webrvr/Doc/0/M8PCVBU8I7GKB9A81TCSAFGC95/Aculyn%2022.pdf.*

* cited by examiner

*Primary Examiner* — Robert A Wax
*Assistant Examiner* — Aradhana Sasan
(74) *Attorney, Agent, or Firm* — Erin Collins

(57) ABSTRACT

An antimicrobial skin composition comprised of an antimicrobial agent, an alcohol, one or more pH sensitive viscosity builders and water. Preferably, the viscosity builders of the present invention are comprised of pH sensitive methacrylic polymers which are alcohol compatible and have pH controlled water solubility. The composition combines the advantages of an antimicrobial agent and an alcohol, and has a viscosity of from 100 cp to 1,000. This viscosity is sufficiently low for purposes of dispensing and applying the preparation, yet sufficiently high to cause the solution to remain in the area of the wound and not flow away or pool under the patient. The preparation further forms a water-resistant film that is difficult to remove during wound irrigation, but can be easily removed upon completion of the procedure. Finally, the preparation is fast drying so as to take advantage of the fast high initial kill properties of alcohol.

11 Claims, No Drawings

ANTIMICROBIAL SKIN PREPARATION

BACKGROUND OF INVENTION

This invention relates to antimicrobial skin preparations. More specifically, it relates to PVP-I/alcohol preparations that are easy to apply but resist flow after application, are fast drying, and form water-resistant but easily removable films.

Antimicrobial skin preparations function to reduce skin infection in surgical and other wounds, including needle punctures. The application of antimicrobial preparations to wounds has become standard practice in hospitals, surgery centers, and medical test laboratories. This application is generally carried out through the use of swabs or sponges to deliver the liquid antimicrobial preparation to the skin. The preparations may be prepared for use in a pre-packaged form (i.e., liquid and swab in a sealed package) or as a separate bottled liquid. Multiple applications of antimicrobial skin preparations are often required, with the preparation either being allowed to dry or blotted dry between applications. Since most current antimicrobial skin preparations are water soluble, reapplication is often necessary after the wound is irrigated with water.

Antimicrobial skin preparations are well known in the art, including those containing iodine complexed with a polymer (iodophors). The polymer is most often polyvinyl pyrrolidone (Povidone). Iodophor preparations typically contain about 7.51-10% by volume of the iodine complex; Povidone-Iodine (PVP-I) solution is one of the most widely accepted preoperative antimicrobials. Solutions containing 5-10% PVP-I are generally recognized as safe. PVP-I solutions form a durable yet water soluble antimicrobial film when dry, and therefore resist pre-mature removal while permitting easy removal with water and mild rubbing. However, most existing iodophor skin preparations are low-viscosity liquids that tend to flow freely after application into areas remote from the wound site. This creates a need for extra care during application and increases the potential for irritation caused by solution pooling under the patient. A product that eliminates the flow problems associated with low-viscosity PVP-I solution is Povidone-Iodine gel (PVP-I gel). PVP-I gel is made by adding a cellulose gel, such as hydroxyethylcellulose, to PVP-I to greatly increase its viscosity to at least 8,000 cp. A PVP-I solution that is gelled with hydroxyethylcellulose is detailed in U.S. Pat. No. 5,137,718. In order to increase the initial kill of bacteria, alcohol can be added to PVP-I gel, as described in U.S. Pat. No. 5,916,882. Gelled PVP-I and PVP-I/alcohol solutions are flow-resistant compositions; however, as a result they are more difficult to dispense and apply than a low viscosity PVP-I solution. Furthermore, solutions in gel form dry slowly, which increases application time and reduces the benefits of the fast acting antimicrobial properties of alcohols in the PVP-I/alcohol gel. Another inherent problem with the current hydrophilic gel preparations is that they are water-soluble and therefore readily rehydrate during wound irrigation or subjection to water-containing body fluids, causing premature removal of the film and interference with surgical drape adhesion during surgical procedures.

Water-resistant films are disclosed in U.S. Pat. Nos. 6,228,354, 5,922,314 and 4,584,192, but the skin preparations that produce these films are low-viscosity and suffer from the flow/pooling problems discussed above. The PVP-I/alcohol solution disclosed in U.S. Pat. No. 6,228,354 has a faster drying time than the PVP-I/alcohol gel, thus taking full advantage of the fast acting antimicrobial properties of alcohol in conjunction with PVP-I. The solution further eliminates interference with surgical drape adhesion caused by gel, and has controlled moisture resistance thereby reducing the likelihood of premature removal by irrigation during procedures. However, in addition to its low viscosity, the film can only be removed with an aqueous alkaline solution and physical rubbing. Similarly, the composition of U.S. Pat. No. 4,584,192 is resistant to removal with water, and can only be removed by certain alcohols which irritate compromised skin.

Finally, most prior art antimicrobial skin preparations use water as a solvent, which slows their drying rate, resulting in slow film formation, flow away from the wound site, and lengthened application process time.

It would be beneficial to have an antimicrobial skin preparation combining the advantages of an antimicrobial agent and an alcohol, which preparation has sufficiently low viscosity for ease of dispensing and application, yet sufficiently high viscosity to cause the solution to remain in the area of the wound and not flow away or pool under the patient; which forms a water-resistant film that is difficult to remove during wound irrigation, but can be easily removed upon completion of the procedure; and which is fast drying so as to take advantage of the fast high initial kill properties of alcohol, limit flow away from the wound site, and decrease application time. Prior to this invention, no single product has been developed to combine the advantages of the various current antimicrobial skin preparations as discussed above.

SUMMARY OF INVENTION

The present invention is an antimicrobial skin preparation having a viscosity of 100 cp to 1000 cp, combining the advantages of an antimicrobial agent and an alcohol. This viscosity level is sufficiently low to allow for easy application and dispensation, but sufficiently high to cause the solution to remain in the area of the wound and not flow away from the prep site or pool under the patient. The viscosity measurements referred to above are made at 25° C. with a Brookfield Viscometer Model LVF, using spindle 2 at 30 rpm. The viscosity of the present invention may be between 150 cp and 700 cp, between 200 cp and 400 cp, or between 200 and 300 cp.

The solution of the present invention further forms a water-resistant film that is difficult to remove during wound irrigation, and has comparable low potential for re-hydration or interference with surgical drape adhesion as standard PVP-I solutions. However, the solution can be easily removed upon completion of the procedure with water and moderate rubbing.

Additionally, the solution of the present invention is fast drying so as to take advantage of the fast high initial kill properties of alcohol, limit flow away from the wound site, and decrease application time.

The solution is further formulated to provide a high level of efficacy with minimum required active concentration, thus reducing solution cost and minimizing irritation. The solution is effective and safe for use on intact skin in single step preparation of phlebotomy, I.V., and surgical sites.

The antimicrobial skin composition of the present invention is comprised of an antimicrobial agent, an alcohol, one or more pH sensitive viscosity builders and water. Surfactants, skin irritation reducers, and buffers may also be included. The active ingredients of the present invention are generally recognized as safe. The use of a pH sensitive viscosity builder eliminates the slow drying and re-hydration problems associated with gel forms of PVP-I and PVP-I/alcohol preparations.

DETAILED DESCRIPTION

The antimicrobial skin composition of the present invention is comprised of, in its most general form, an antimicrobial agent, an alcohol, one or more pH sensitive viscosity builders and water. Preferably, the antimicrobial agent is complexed with a polyvinyl lactam, and more preferably the antimicrobial agent constitutes PVP-I. Suitable alcohols for the solution of the present invention include but are not limited to ethanol and isopropanol. Isopropanol is preferred, as it is more efficient than ethanol in dissolving skin oils.

The viscosity builders in the solution are alcohol compatible and have pH controlled water solubility, and are preferably methacrylic polymers. The preferred viscosity builders include acidic acrylic polymers such as Acrylates/C10-30 Alkyl Acrylate Crosspolymer, Acrylates/Beheneth-25 Methacrylate Copolymer, Acrylates Copolymer, Acrylates/Steareth-20 Methacrylate Copolymer and Carbomer. A more preferred viscosity builder is the Acrylates/Steareth-20 Methacrylate Copolymer, which is available under the trade name of Aculyn 22 from Rohm and Haas. Aculyn 22 is supplied by Rohm and Haas at a polymer solids concentration of 30%, with a pH of about 3.0. Acidic acrylic polymers normally function as viscosity builders that become more water-soluble as they are neutralized; the water solubility thereof is limited in the present invention because of the relatively low pH of the solution. While the polymer is insoluble in water at low pH, it is compatible with alcohol regardless of the pH level thereof, and therefore the polymer is especially suitable in the low pH solution of the present invention. Furthermore, viscosity builders having pH controlled water solubility decrease the water solubility of the prep film of the present invention, but allow for easy removal by mild physical rubbing. The main mechanism of Aculyn 22 in building viscosity for the solution of the present invention is its associative thickening properties, caused by physical forces between particles of Aculyn 22 and the solution.

Preferably, the solution contains 5-10% by weight complexed antimicrobial agent, 60-95% by volume alcohol, 1-5% by solids weight polymer pH sensitive viscosity builder, and water. As regards the alcohol, when using ethanol it should comprise about 60-95% of the volume of the entire solution, whereas isopropanol should comprise about 70-91.3% of the volume of the entire solution. The preferred solution has a pH range from about 1.5 to 6.5, and a specific gravity range of about 0.790 to 0.990 depending upon the applicable concentrations of the actives and excipient, if any. The pH may also be in the range between 3 and 4. The solution of the present invention may also include a skin irritation reducer (e.g., glycerin), a surface tension adjuster (e.g., a nonionic surfactant such as Nonoxynol-9), a synergistic secondary thickener (e.g., polyvinyl pyrrolidone), acid and base pH adjusters (e.g., phosphoric acid and aminomethyl propanol), buffers and/or additional viscosity builders.

A more preferred embodiment of the invention includes about 5-10% by weight PVP-I; about 70-91% by volume isopropanol; about 0.2%-0.3% by weight aminomethyl propanol; about 0.01% to 1.0% by weight phosphoric acid; 0.1%-5% by weight glycerin; 0.1% to 1.0% by weight nonionic surfactant Nonoxynol-9; and 2%-4% pH sensitive methacrylic polymer viscosity builder selected from acidic acrylate polymers which are commonly used as viscosity builders.

A final preferred antimicrobial skin preparation embodiment of the present invention comprises, by weight: 7.5% PVP-I, 0.75% available iodine (USP/EP Grade); 64.5% isopropanol (USP/EP Grade); 2.4% Acrylates/Steareth-20 Methacrylate Copolymer; 0.27% aminomethyl propanol 95%; 0.06% phosphoric acid (75%); and water. The pH of this preferred embodiment of the present invention is approximately 3.5, the viscosity is approximately 250 cp, and the specific gravity is approximately 0.889.

The composition of the present invention is preferably manufactured by combining a minimal amount of the alcohol and sufficient amount of the water to provide volume to blend in the antimicrobial agent, if the same is provided in powdered form. As there is some risk of ignition of suspended dust particles when adding a powdered antimicrobial agent, the preliminary alcohol content should be minimal and the dust particles should be added to avoid forming a cloud of finely dispersed particles over the batch. The viscosity builder is then preferably diluted in water and added slowly to the solution. Any additional alcohol can then be added to the solution, as well as any desirable elements such as glycerin and base pH adjusters. Each element should be added slowly, and mixed well into the solution so that the solution is homogeneous prior to the addition of a subsequent element.

The invention claimed is:

1. An antimicrobial skin composition having a viscosity in solution of between about 100 to 1,000 cps at 25° C. measured with a Brookfield viscometer, model LVF, using spindle 2 at 30 rpm, consisting of:
   povidone-iodine;
   60-95% by volume alcohol;
   one or more pH sensitive methacrylic polymers, in an amount sufficient to build the viscosity of the composition in solution to between about 100 to 1,000 cps at 25° C. measured with a Brookfield viscometer, model LVF, using spindle 2 at 30 rpm, wherein at least one of the pH sensitive methacrylic polymers is acrylates/steareth-20 methacrylate copolymer;
   aminomethyl propanol;
   phosphoric acid; and
   water.

2. The composition of claim 1, wherein at least one of the alcohols is selected from the group consisting of: ethanol and isopropanol.

3. The composition of claim 1, wherein the viscosity of the composition is between 150 and 700 cps at 25° C. measured with a Brookfield viscometer, model LVF, using spindle 2 at 30 rpm.

4. The composition of claim 1, wherein the viscosity of the composition is between 200 and 400 cps at 25° C. measured with a Brookfield viscometer, model LVF, using spindle 2 at 30 rpm.

5. The composition of claim 1, wherein the pH of the composition is from about 1.5 to 6.5.

6. An antimicrobial skin composition having a viscosity in solution of between about 150 to 700 cps at 25° C. measured with a Brookfield viscometer, model LVF, using spindle 2 at 30 rpm, consisting of:
   (a) 5-10% by weight povidone-iodine,
   (b) 60-95% by volume alcohol,
   (c) pH sensitive acidic acrylic polymers, comprising acrylates/steareth-20 methacrylate copolymer,
   (d) aminomethyl propanol;
   (e) phosphoric acid;
   (f) and water.

7. The composition of claim 6, wherein the alcohol is isopropanol and is contained at 70-91.3% by volume.

8. The composition of claim 6 or 7, wherein the pH sensitive acidic acrylic polymer is acrylates/steareth-20 methacrylate copolymer.

9. An antimicrobial skin composition having a viscosity in solution of between 100 and 1,000 cps at 25° C. measured with a Brookfield viscometer, model LVF, using spindle 2 at 30 rpm, consisting of:
(a) 5-10% by weight povidone-iodine,
(b) 70-91% by volume isopropanol,
(c) acidic acrylic polymer, wherein the type and amount of said acrylic polymers are selected to increase the viscosity of the composition in solution to between about 100 to 1,000 cps at 25° C. measured with a Brookfield viscometer, model LVF, using spindle 2 at 30 rpm,
(d) 0.2%-0.3% w/w aminomethyl propanol;
(e) 0.01% to 1.0% w/w phosphoric acid;
(f) water.

10. The composition of claim 9, wherein the pH of the composition is approximately 3 to 4 and the viscosity is between 200 and 300 cps at 25° C. measured with a Brookfield viscometer, model LVF, using spindle 2 at 30 rpm.

11. An antimicrobial skin composition having a viscosity in solution of between about 100 to 1,000 cps at 25° C. measured with a Brookfield viscometer, model LVF, using spindle 2 at 30 rpm, consisting of:
povidone-iodine;
one or more alcohols;
one or more pH sensitive methacrylic polymers, comprising acrylates/steareth-20 methacrylate copolymer, in an amount sufficient to build the viscosity of the composition in solution to between about 100 to 1,000 cps at 25° C. measured with a Brookfield viscometer, model LVF, using spindle 2 at 30 rpm;
pH adjusters selected from the group consisting of: aminomethyl propanol and phosphoric acid, and combinations thereof, in an amount sufficient to bring the solution into a pH range of between 1.5 and 6.5;
water; and
additives selected from the group consisting of: skin irritation reducers, surface tension adjusters, and buffers, and combinations thereof.

* * * * *